(12) United States Patent
Crawford et al.

(10) Patent No.: US 11,957,710 B2
(45) Date of Patent: Apr. 16, 2024

(54) WOUND-CARE COMPOSITION AND METHOD OF USE

(71) Applicants: Mary Crawford, Sachse, TX (US); Jonathon Crawford, Sachse, TX (US)

(72) Inventors: Mary Crawford, Sachse, TX (US); Jonathon Crawford, Sachse, TX (US)

( * ) Notice: Subject to any disclaimer, the term of this patent is extended or adjusted under 35 U.S.C. 154(b) by 0 days.

(21) Appl. No.: 17/714,465

(22) Filed: Apr. 6, 2022

(65) Prior Publication Data

US 2023/0321139 A1    Oct. 12, 2023

(51) Int. Cl.

| | | |
|---|---|---|
| *A61K 33/06* | (2006.01) | |
| *A61K 9/00* | (2006.01) | |
| *A61K 31/045* | (2006.01) | |
| *A61K 31/15* | (2006.01) | |
| *A61K 31/17* | (2006.01) | |
| *A61K 31/34* | (2006.01) | |
| *A61K 31/345* | (2006.01) | |
| *A61K 31/473* | (2006.01) | |
| *A61K 31/79* | (2006.01) | |
| *A61K 47/06* | (2006.01) | |
| *A61K 47/46* | (2006.01) | |
| *A61P 17/02* | (2006.01) | |

(52) U.S. Cl.
CPC ............ *A61K 33/06* (2013.01); *A61K 9/0014* (2013.01); *A61K 31/045* (2013.01); *A61K 31/15* (2013.01); *A61K 31/17* (2013.01); *A61K 31/34* (2013.01); *A61K 31/345* (2013.01); *A61K 31/473* (2013.01); *A61K 31/79* (2013.01); *A61K 47/06* (2013.01); *A61K 47/46* (2013.01); *A61P 17/02* (2018.01)

(58) Field of Classification Search
CPC .......... A61K 8/26; A61K 33/06; A61K 47/06; A61K 31/17
See application file for complete search history.

(56) References Cited

U.S. PATENT DOCUMENTS

| | | | | |
|---|---|---|---|---|
| 5,550,112 | A * | 8/1996 | Gallina ................... | A61P 17/00 514/54 |
| 2015/0359819 | A1* | 12/2015 | Speaker ................. | A61K 33/06 424/618 |
| 2016/0199343 | A1* | 7/2016 | De Visscher ........ | A61K 9/7023 424/447 |

FOREIGN PATENT DOCUMENTS

| | | | | |
|---|---|---|---|---|
| CN | 102210651 | A | * 10/2011 | |
| CN | 102219430 | A | * 10/2011 | ............. C04B 18/08 |
| EP | 0649656 | A1 | * 4/1995 | ............. A61K 31/47 |

OTHER PUBLICATIONS

Farid et al (Geriatric Nursing, 2011, vol. 32, pp. 85-95) (Year: 2011).*
CN-102219430-A (Google English translation, downloaded Jun. 2023) (Year: 2023).*
EP-0649656-A1 (Google English translation, downloaded Jun. 2023) (Year: 2023).*
CN-102210651-A (Google English translation, downloaded Jun. 2023) (Year: 2023).*
Cosmetics Info (Potassium Alum, 2023, https://www.cosmeticsinfo.org/ingredients/potassium-alum/) (Year: 2023).*
Amazon Listing 01—Amazon Brand—Sunburn Relief Gel with Aloe Vera, 8 Fluid Ounce, available on the internet at https://www.amazon.com/Sunburn-Relief-Aloe-Fluid-Ounce/dp/B07WHYG7WX, accessed on Sep. 9, 2021 (9 pages).
Amazon Listing 02—Amazon Brand—Solimo 10% Povidone Iodine Solution First Aid Antiseptic, 8 Fluid Ounce (Pack of 4), available on the internet at https://www.amazon.com/Amazon-Brand-Povidone-Solution-Antiseptic/dp/B07CL85LKW, accessed on Sep. 9, 2021 (8 pages).
Amazon Listing 03—Amazon Brand—Solimo Petroleum Jelly White Pertolatum Skin Protectantm Unscented, 7.5 Ounce, available on the internet at https://www.amazon.com/Amazon-Brand-Petroleum-Petrolatum-Protectant/dp/B07SKXXPMZ/ref=pd_vtp_1/135-6476469-4814556?pd_rd_w=pYPFN&pf_rd_p=016e3697-91be-4dc2-9533-ef9350e7e73d&pf_rd_r=GSDN15QN4KQ6EFE4PR88&pd_rd_r=f78f96db-fcf2-446a-87c1-3b307babfde0&pd_rd_wg=rCXhT&pd_rd_i=B07SKXXPMZ&psc=1, accessed on Sep. 9, 2021.
Amazon Listing 04—Horse Health Pine Tar, 32 fl oz, available on the internet at https://www.amazon.com/Horse-Health-Pine-Tar-32/dp/B000HHHDNS/ref=asc_df_B000HHHDNS/?tag=hyprod-20&linkCode=df0&hvadid=198093497902&hvpos=&hvnetw=g&hvrand=9706864589019934 90&hvpone=&hvptwo=&hvqmt=&hvdev=c&hvdvcmdl=&hvlocint=&hvlocphy=9026938&hvtargid=pla-353124975790&psc=1, accessed on Sep. 9, 2021 (6 pages).
Amazon Listing 05—MB Herbals Alum Powder 250 Gram | Potassium Alum Powder | Purified Alum Powder Through Shodhan Purification Process | Food Preservative | Helps in Canker Sores, available on the internet at https://www.amazon.com/MB-Herbals-Potassium-Traditional-Purification/dp/B07VV9HFTZ, accessed on Sep. 9, 2021 (5 pages).
Amazon Listing 06—Squire Fura-Zone Ointment by Durvet 1 Pound, available on the internet at https://www.amazon.com/Squire-Fura-Zone-Ointment-Durvet-Pound/dp/B001CCZQAY, accessed on Sep. 9, 2021 (5 pages).
Amazon Listing 07—Farnam Antiseptic Wound Dressing and Gall Lotion | Quick-Drying Lotion | for Horses, Ponies and Dogs | 4 oz, available on the internet at https://www.amazon.com/Farnam-Lotion-Wound-Dressing-Antiseptic/dp/B000HHQ2R6, accessed on Sep. 9, 2021 (5 pages).

* cited by examiner

*Primary Examiner* — Mark V Stevens
(74) *Attorney, Agent, or Firm* — Stephen Y. Liu; Carstens, Allen & Gourley, LLP

(57) ABSTRACT

Wound-care composition and method of use. The composition comprises: a substrate; potassium alum; and urea. The potassium alum makes up 10.27 wt. % of the composition within a tolerance of +/- 50%; and the urea makes up 0.12 wt. % of the composition within a tolerance of +/- 50%. The method comprises applying the composition to a wound on a non-human animal.

19 Claims, 1 Drawing Sheet

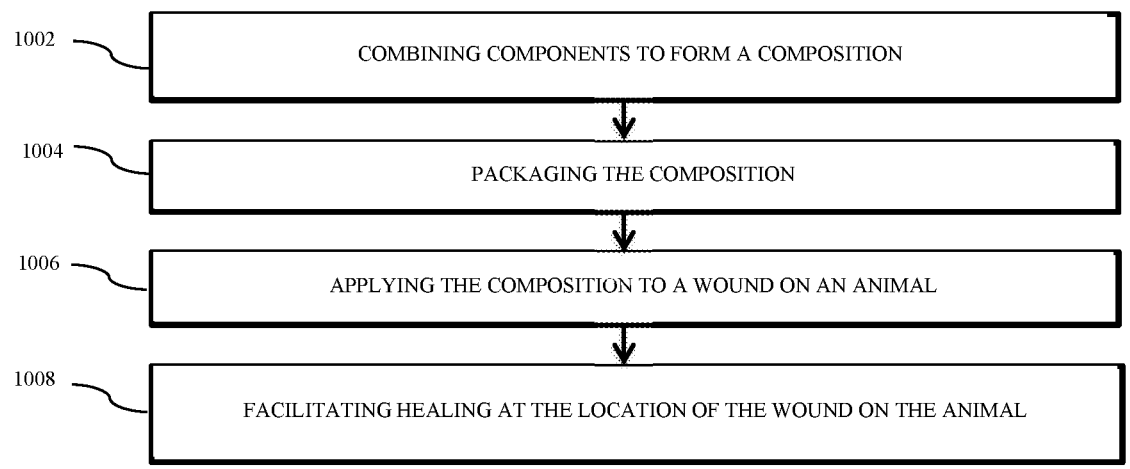

WOUND-CARE COMPOSITION AND METHOD OF USE

BACKGROUND

CROSS-REFERENCE TO RELATED APPLICATIONS

None.

TECHNICAL FIELD

The present invention relates to wound-care compositions that can be used to reduce scarring in animals, for example, horses.

BACKGROUND

Existing wound-care compositions do not sufficiently reduce scarring. This can be undesirable, especially for animals that may be evaluated based on the appearance of their skin and hair. For example, hair can grow back inconsistently over a wound that results in scar tissue.

SUMMARY OF THE INVENTION

In one aspect, a wound-care composition is provided. The composition comprises: a substrate; potassium alum; and urea. The potassium alum makes up 10.27 wt. % of the composition within a tolerance of +/−50%; and the urea makes up 0.12 wt. % of the composition within a tolerance of +/−50%.

In a second aspect, a method is provided. The method comprises applying the composition to a wound on a non-human animal.

Other aspects, embodiments and features of the invention will become apparent from the following detailed description of the invention when considered in conjunction with the accompanying drawings. The accompanying figures are schematic and are not intended to be drawn to scale. In the figures, each identical, or substantially similar component that is illustrated in various figures is represented by a single numeral or notation. For purposes of clarity, not every component is labeled in every figure. Nor is every component of each embodiment of the invention shown where illustration is not necessary to allow those of ordinary skill in the art to understand the invention.

BRIEF DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

FIG. 1 is a flow chart illustrating several method steps for making and using a composition.

DETAILED DESCRIPTION

This disclosure describes compositions that can be topically applied to a wound on an animal, for example, a horse. The disclosure also describes methods of making the compositions and methods of using the compositions.

The compositions can be used to support healing of wounds, to reduce the likelihood of infection, to reduce scarring, facilitate regrowth of hair, and to provide a wounded region with an appearance after healing that is more similar to adjacent unwounded regions when compared to how the wounded region would appear after healing in the absence of the compositions.

An embodiment of a composition in accordance with this disclosure will now be described with reference to Table 1. The values in the tables may not sum to 100% in all cases due to rounding.

TABLE 1

Illustrative Composition

| COMPONENT OF COMPOSITION | Mass (g) IN COMPOSITION (Rounded) | Wt. % IN COMPOSITION (Rounded) |
| --- | --- | --- |
| Pine tar | 946 | 38.87 |
| Petrolatum | 226.13 | 9.29 |
| Additional Ingredients | 981.07 | 40.32 |
| Substrate and Additional Ingredient Subtotal | 2153.2 | 88.48 |
| Potassium Alum | 250 | 10.27 |
| Povidone-iodine | 23.7 | 0.97 |
| Acriflavin | 0.047 | 0.002 |
| Methyl Violet | 0.80 | 0.033 |
| Technical Furfural | 0.91 | 0.037 |
| Urea | 2.83 | 0.12 |
| Nitrofurazone | 0.91 | 0.037 |
| Lidocaine HCl | 1.13 | 0.046 |
| Active Ingredients, Excluding Base and Additional Ingredients | 280.33 | 11.52 |
| COMPOSITION TOTAL | 2433.53 | 100.00 |

As can be seen, the composition of Table 1 comprises base components including pine tar and petrolatum and additional ingredients that make up approximately 88.48 wt. % of the illustrative composition. The composition of Table 1 also comprises listed active ingredients including potassium alum, povidone-iodine, acriflavine, methyl violet, technical furfural, urea, nitrofurazone, and lidocaine HCl. These listed active ingredients are mixed with the base components and additional ingredients to provide the composition. Although the term active ingredients can refer to ingredients with a particular function, other components can also provide functions, including functions similar to the functions of active ingredients. For example, pine tar can be an antiseptic. In some embodiments, the active ingredients can be provided in the form of sub-formulations that comprise the active ingredients and the additional ingredients. As an example, Table 2 illustrates how a composition that approximately matches the composition of Table 1 can be provided by mixing commercially available formulations.

TABLE 2

Illustrative Composition

| Sub-Formulation | Mass (g) of Sub-Formulation in Composition | Wt. % Sub-Formulation in Composition | Component in Sub-Formulation | Wt. % of Component in Sub-Formulation | Mass (g) of Component in Composition |
|---|---|---|---|---|---|
| Pine Tar | 946 | 38.87 | Pine tar | 100 | 946 |
| Petrolatum | 226.13 | 9.29 | Petrolatum | 100 | 226.13 |
| Substrate Subtotal | 1172.13 | 48.2 | Not Applicable | Not Applicable | Not Applicable |
| Potassium Alum Powder | 250 | 10.27 | Potassium Alum | 100 | 250 |
| Povidone-iodine solution 10% | 237 | 9.74 | Povidone-iodine | 10 | 23.7 |
| Antiseptic Wound Dressing and Gall Lotion for Horses, Ponies and Dogs | 94.4 | 3.88 | Acriflavin | 0.05 | 0.047 |
| | | | Methyl Violet | 0.85 | 0.80 |
| | | | Technical Furfural | 0.96 | 0.91 |
| | | | Urea | 3.0 | 2.83 |
| Antibacterial Preparation for Topical Application to Horses | 454 | 18.66 | Nitrofurazone | 0.2 | 0.91 |
| Sunburn relief gel with aloe vera and lidocaine HCl | 226 | 9.29 | Lidocaine HCl | 0.5 | 1.13 |
| Sub-Formulations Subtotal (including Active Ingredients and Additional Ingredients) | 1261.4 | 51.8 | Not Applicable | Not Applicable | Not Applicable |
| COMPOSITION TOTAL | 3414.6 | 100.0 | Not Applicable | Not Applicable | Not Applicable |

As can be seen, the mass of a sub-formulation in the composition can be multiplied by the weight percentage of a particular ingredient in the sub-formulation to obtain the mass of the particular ingredient in the composition. For example, Povidone-iodine makes up 10 wt. % of the Povidone-iodine solution and there are 237 grams of the Povidone-iodine solution in the composition. Therefore, there are 23.7 grams of Povidone-iodine in the composition.

Examples of formulations of pine tar; petrolatum; potassium alum powder; povidone-iodine solution 10%; an antiseptic wound dressing and gall lotion for horses, ponies and dogs; antibacterial preparation for topical application to horses; and sunburn relief gel with aloe vera and lidocaine HCl are described in non-patent literature listed in and attached to the Information Disclosure Sheet (IDS) filed with this patent application. The identifying information and technical disclosure (including without limitation identifying information, manufacturing information, ingredients, compositional information, and physical properties for the formulations listed in this paragraph) of the non-patent literature documents (including without limitation the documents whose description includes Amazon Listing 01, Amazon Listing 02, Amazon Listing 03, Amazon Listing 04, Amazon Listing 05, Amazon Listing 06, and Amazon Listing 07) in the IDS filed with this patent application are hereby incorporated by reference in their entireties as examples of this disclosure, but the customer comments, customer questions, reviews and asserted related products of the non-patent literature are not incorporated by reference in this disclosure.

It should be understood that Table 1 and Table 2 and the listed examples of sub-formulations provide one example of how a composition as described in this disclosure can be provided. However, as is evident, other compositions can also be created in accordance with this disclosure.

With reference to FIG. 1, a combined method can comprise several steps. A first step comprises, combining 1002 components (e.g., any component described in this disclosure) to form a composition. The components can be mixed using a mechanical mixer or mixed by hand, for example, with a spoon. In some embodiments, the components are mixed for approximately 5 minutes (e.g., 4 to 6 minutes) to form the composition. In some embodiments, the components are mixed until the components appear visibly well-mixed or homogenous at a top surface of the mixed components. In some embodiments, the components can be combined in any order. In some embodiments, at least one dry component (e.g., potassium alum powder) is added to at least one of the components that is a liquid (e.g., pine tar, petrolatum, an antiseptic, povidone-iodine solution, an antibacterial, a pain relief composition, acriflavin, methyl violet, nitrofurazone, furfural, a composition comprising any of these components, or any combination of the foregoing). In some embodiments, the liquid components of the composition are combined first, and the dry components are added to the combined liquid components of the composition. The components can be mixed until the at least one dry component is well dispersed in at least one liquid component or any combination (e.g., mixture) of the liquid components of the composition.

In some embodiments, a heating step can occur before the combining step, during the combining step, or both before and during the combining step. As an example, at least one of the components (e.g., the pine tar) can be heated, for example, to a temperature less than the boiling temperature of the component (e.g., pine tar) at ambient pressure (e.g., 101.325 kPa). In some embodiments, the at least one of the components can be heated from 65.5 to 93.3° C. (150 to 200° F.) optionally over approximately 5 minutes (e.g., 4 to 6 minutes). Because some of the components (e.g., pine tar) can be so viscous at ambient temperature (e.g., 25° C.), the heating step can be useful to decrease viscosity and increase the flowability and ease of combining the components.

With reference again to FIG. 1, a second step comprises packaging 1004 the composition (e.g., in a package, for example, a tube, a jar or any other container, which container can also include a mechanism for opening and resealing the container, for example, a lid (e.g., a screw on cap). In some embodiments, a package for the composition can comprise, contain or be packaged with an applicator (e.g., a spoon, which can be wooden or plastic). The applicator can be used to apply the composition to a wound, smooth out the composition to a desired thickness over the wound, so that a human applying the composition to an animal can avoid contacting the composition, or any combination thereof).

A third step comprises applying 1006 the composition to a wound on an animal. Optionally, the composition can be applied to the wound to coat the wound with a layer that is 1 mm to 12.7 mm, 3.175 to 6.35 mm (⅛ to ¼ inch) or 3.175 to 12.7 mm (⅛ to ½ inch) in thickness. In some embodiments, a thin layer of the composition is used, for example, approximately 1 mm or approximately ⅛ inch or approximately ¼ inch. In some embodiments, a thicker layer of the composition is used to coat the wound, for example, approximately ¼ inch or ½ inch. This can be useful, for example, in situations where some of the composition is expected to be rubbed off or washed away, for example, by water and/or where the composition is intended to be left in place for more than 1 day, for example, 2 to 14 days, 2 to 7 days, or 3 to 5 days. In some embodiments, the composition can be left in place, for example, with or without a bandage being placed over (e.g., wrapped around) the composition and the wound for more than 1, 2, 3, 4, 5, 6, 7, 8, 9, 10, 11, 12, or 13 days and up to 2, 3, 4, 5, 6, 7, 8, 9, 10, 11, 12, 13 or 14 days. In some embodiments, the durability of the composition and its ability to remain in place and provide protection and/or enhance healing for a wound is advantageous in comparison to existing compositions.

A fourth step comprises facilitating healing 1008 (e.g., reducing the risk of infection, avoiding infection, killing, neutralizing or deactivating pathogens so that they cannot cause infection, promoting healthy tissue growth, promoting repair of the skin, reducing scarring, avoiding scarring or any combination thereof) at the location of the wound on the animal. In some embodiments, the animal is a non-human animal, mammal, horse, animal that is not intended for human consumption, or any combination thereof.

As each of the steps illustrated in FIG. 1 can be an independent method, it is possible to form additional methods by combining any one of the steps with any other step or any combination of other steps described in this disclosure.

With respect to combining 1002 components (e.g., any component described in this disclosure) to form a composition, the composition can be formed by combining (e.g., mixing) components (e.g., sub-formulations, individual ingredients or any combination thereof) in any mass ratios disclosed herein or to provide a composition with any weight percentage of a component or any combination of components disclosed in this disclosure.

The components of the composition can be mixed in any order. In some embodiments the components may be mixed for approximately 20 minutes using a mixer. A homogeneous mixture is an example of a sufficiently well-mixed mixture, but a completely homogeneous mixture is not required. For purposes of providing consistent performance of the composition, it can be useful if the concentration of any ingredient throughout the composition is constant within a desired variance for substantially the entire volume of the composition. The key idea is that any typical amount of the composition that is discharged from a package containing the composition and applied to a wound would facilitate healing. For example, if the entire composition or approximately the entire composition is discharged from an orifice in a container and 5 mL samples or about 5 mL are taken starting at or approximately at initial discharge, 10% vol. discharge, 20% vol. discharge, 30% vol. discharge, 40% vol. discharge, 50% vol. discharge, 60% vol. discharge, 70% vol. discharge, 80% vol. discharge, and 90% vol. discharge, all relative to the total volume of the composition in the container, it can be useful if the concentration of a component of the composition, a selection of components of the composition, or each of the components in the composition varies by no more than +/−25, 20, 15, 10, 9, 8, 7, 6, 7, 5, 4, 3, 2 or 1% from the average concentration of the component, selection of components or each of the components in the composition as a whole.

An example of a wound-care composition comprises: a substrate; potassium alum; and urea. The potassium alum can make up 10.27 wt. % of the composition within a tolerance of +/−50%; and the urea can make up 0.12 wt. % of the composition within a tolerance of +/−50%. In some embodiments, without being bound by theory, it is believed that the potassium alum can help to close the wound.

In some embodiments, the composition or the substrate comprises pine tar and petrolatum. The pine tar can make up 38.87 wt. % of the composition within a tolerance of +/−50%, and wherein the petrolatum can make up 9.29 wt. % of the composition within a tolerance of +/−50%. In some embodiments, the pine tar can help increase the viscosity, or reduce the spreadability, or reduce the flowability, or reduce the malleability of the composition. In some embodiments, the pine tar can help keep the composition in place after the composition is applied to a wound. In some embodiments, the petrolatum can help provide additional spreadability and/or flowability and/or malleability to the composition compared to a composition without the petrolatum. In some embodiments, the mass ratio of the petrolatum to pine tar can be increased to increase the spreadability and/or flowability and/or malleability of the composition and the mass ratio can be decreased to decrease the spreadability and/or flowability and/or malleability of the composition and increase the durability of the composition and its ability to remain in place. In some embodiments, the pine tar and/or the petrolatum can help increase the water resistance of the composition, for example, by helping to prevent the composition from being easily washed off by water (e.g., rain, moisture, etc.). Optionally, the term "pine tar" can be replaced by "tree tar" or "tar" throughout this disclosure to form additional embodiments of the composition. Optionally, the term "tree tar" can be replaced by "tar" throughout this disclosure to form additional embodiments of the composition.

In some embodiments, the potassium alum is a potassium alum powder.

In some embodiments, the composition comprises at least one antiseptic, optionally the at least one antiseptic comprising povidone-iodine, acriflavin, methyl violet, ethyl alcohol, or any combination thereof. The antiseptic can help prevent infection of the wound.

In some embodiments, the composition comprises at least one antibacterial, optionally the at least one antibacterial comprising nitrofurazone, methyl violet, ethyl alcohol, or any combination thereof.

In some embodiments, the composition comprises at least one antiviral, optionally the at least one antiviral comprising povidone-iodine, ethyl alcohol or any combination thereof.

In some embodiments, the composition comprises at least one fungicide, optionally the at least one fungicide comprising povidone-iodine, methyl violet, furfural, ethyl alcohol, or any combination thereof.

In some embodiments, the composition comprises at least one nematicide, optionally the at least one nematicide comprising methyl violet, furfural, or any combination thereof.

In some embodiments, the composition comprises at least one pain reliever.

In some embodiments, povidone-iodine can make up 0.97 wt. % of the composition within a tolerance of +/−50%.

In some embodiments, acriflavin can make up 0.002 wt. % of the composition within a tolerance of +/−50%. The acriflavin can be a mixture of 3,6-Diamino-10-methylacridinium methylacridinium chloride and 3,6-acridinediamine.

In some embodiments, methyl violet can make up 0.03 wt. % of the composition within a tolerance of +/−50%. The methyl violet can be Methyl Violet 2B, Methyl Violet 6B, Methyl Violet 10B or any combination thereof.

In some embodiments, nitrofurazone can make up 0.04 wt. % of the composition within a tolerance of +/−50%.

In some embodiments, furfural can make up 0.04 wt. % of the composition within a tolerance of +/−50%.

In some embodiments, the pain reliever is lidocaine HCl. The lidocaine HCl can make up 0.05 wt. % of the composition within a tolerance of +/−50%.

In some embodiments, the composition comprises ethyl alcohol. The ethyl alcohol can make up 1 to 4 wt. % of the composition.

In some embodiments, the composition comprises water. The water can make up 2 to 10 wt. % of the composition.

In some embodiments, the composition comprises C12-13 Pareth-9. The C12-13 Pareth-9 can make up 1 to 8 wt. % of the composition.

In some embodiments, the composition comprises at least one polyethylene glycol. The at least one polyethylene glycol can make up 18.7 wt. % of the composition within a tolerance of +/−50%.

In some embodiments, the composition is formulated to provide a reduction in scarring in a wound on a horse when a layer of the composition is topically applied to the wound within 1, 2, 3, 4, 6, 12, or 24 hours of the time that the wound occurred. The reduction in scarring is deemed to be achieved if:

the layer of the composition is applied to a treated portion of the wound and the treated portion of the wound is covered with a first bandage;
  a second bandage is applied to an untreated portion of the wound that is not treated by application of the composition, the second bandage being identical to the first bandage, and dimensions (e.g., length, width, area, shape or any combination thereof) of the untreated portion and the treated portion are equal;
  every 24 hours (or optionally every 2, 3, 4, 5, 6, 7, 8, 9, 10 days, where a day is equal to 24 hours): the first bandage or a replacement bandage for the first bandage is removed from the treated portion of the wound, a new layer of the composition is applied to the treated portion of the wound, and the treated portion of the wound is covered with a replacement bandage for the first bandage;
  every 24 hours (or optionally every 2, 3, 4, 5, 6, 7, 8, 9, 10 days, where a day is equal to 24 hours): the second bandage or a replacement bandage for the second bandage is removed from the untreated portion of the wound, and the untreated portion of the wound is covered with a replacement bandage for the second bandage; and
  30 days after the application of the composition, the area of scar tissue corresponding to the treated portion of the wound is smaller than (e.g., no more than 95%, 90%, 80%, 70%, 60%, 50%, 40%, 30%, 20%, 10% or 5% of) the area of scar tissue corresponding to the untreated portion of the wound. In some embodiments, the composition is water-resistant. In some embodiments, if water is applied to the composition and alternative compositions for dressing wounds under the same conditions, less (if any) of the composition will be washed away compared to any or all of the alternative compositions. Accordingly, even if an existing product might work as well as the presently disclosed composition under ideal conditions, the composition disclosed herein can work better under conditions encountered in the real world, including rain, water, moisture, and contact with items that can remove or displace the composition from a wound. In some embodiments, the composition can be applied to wounds that are not easy (or that are not practical or that are even impossible) to cover with a bandage (e.g., wrap bandage, adhesive bandage, veterinarian tape or any combination thereof). Accordingly, the characteristics of the composition, for example, increased viscosity, increased durability, water-resistance, or any combination thereof can be useful to help maintain the composition in place over a wound even when a bandage cannot be applied. Additionally, the characteristics of the composition can be useful to increase the time between applications of the composition to a wound while the wound is healing. As another example, in comparison to other existing wound care compositions, the composition can decrease the number of times that a wound needs to be treated (e.g., by applying a wound care composition to the wound) while the wound is healing.

In some embodiments, the composition comprises additional ingredients selected from the group consisting of water, propylene glycol, glycerin, Aloe barbadensis leaf juice, triethanolamine, isopropyl alcohol, polysorbate 80, carbomer, phenoxyethanol, benzyl alcohol, menthol, disodium EDTA, blue 1, yellow 5, C12-13 Pareth-9, citric acid, disodium phosphate, sodium hydroxide, water soluble polyethylene glycols, ethyl alcohol, and sodium propionate.

Now an example of a method for using the composition will be described. The method can comprise: applying the composition to a wound on a non-human animal.

In some embodiments, the method comprises: using the composition to promote healing at the location of the wound on the non-human animal.

GENERALIZED EXAMPLES

A few generalized examples follow. The examples are based on or inspired by, but not necessarily identical to, examples of actual use of a composition similar to or included in the compositions described in this disclosure.

As a first generalized example, Horse A has a habit of pawing things, including barbed wire fence. As a result, a soft portion of Horse A's front paws become injured. To treat Horse A, the composition is applied generously to the injured paws to provide a thick layer of the composition. Next, the injured paws, with the composition over the wound, are each wrapped with veterinarian wrap or bandage (e.g., veterinarian tape, which is self-adherent and similar to an elastic or rubbery bandage or elastic or rubbery wrap, for example, an ACE brand bandage, but intended for use with horses or other animals). Then, a boot is made for each of the horse's paws. The boot is made by wrapping duct tape around the veterinarian tape, which is wrapped around each hoof, including the wound on each hoof, which wound is covered with the composition. Each boot, made of tape, is wrapped around each injured hoof, including the bottom of each injured hoof). The composition, the veterinarian tape, and the boot of duct tape are left in place for approximately 5 days, or perhaps 3-5 days depending on the severity of the conditions to which the composition, veterinarian tape and boot are subjected. Next, the boot is examined and cleaned to a desired level of cleanliness, if applicable. Then, an additional amount of the composition is applied to the wound, which is again wrapped with veterinarian tape and duct tape to form another boot of duct tape as previously described. This process of examining the wound, cleaning the wound as desired, applying an additional amount of the composition, and wrapping the composition with veterinarian tape and duct tape can be repeated every 3 to 5 days for approximately 1 week to 2 weeks until the wound heals. Advantageously, the wound can heal with no scar or a reduced scar compared to the size of the scar that would have occurred without use of the composition.

Also, while the prior example has been described using a boot (which can be made of duct tape or another material), a boot is not necessary in all circumstances. In some embodiments, the compositions disclosed herein can be applied to a wound with or without any bandage or wrap (e.g., veterinarian wrap) covering the composition and the wound, with or without a boot (e.g., made of duct tape or any other material) surrounding the bandage or wrap, or any combination thereof.

As another generalized example, Horse A sits on a T-post and has a gaping open wound approximately 6-7 inches long. It is not practical to wrap the wound. A composition (e.g., a composition included in this disclosure) is applied to the wound without wrapping the wound with a wrap or bandage (e.g. veterinarian tape) or providing any other covering for the composition on the wound. The horse is monitored in a pasture. Over time, the wound gets thinner. Whenever it appears that the composition may be rubbed or washed off or otherwise getting thinner, the composition is reapplied to maintain a protective layer of the composition over the wound. The composition is reapplied every 3 to 5 days until the wound appears to be healed. Hair begins to grow back in the region on the skin where the wound occurred.

In some cases, a wound that is covered with the composition but not also wrapped, bandaged or otherwise covered with a protective layer of material can take longer to longer to heal compared to a wound that is covered with the composition and also wrapped, bandaged or covered with the protective layer of material. Nonetheless, in some embodiments, the composition is flowable or spreadable enough (e.g., at 25° C.) to be applied to a wound and durable enough to be applied to a wound on essentially any portion of skin on an animal, even if the wound cannot be covered. In some embodiments, the increased durability of the composition, including without limitation weather-resistance (e.g., resistance to displacement or removal due to water or water moisture), resistance to displacement or removal due to abrasion or contact with an object can help reduce the size of any scar that results after a wound when compared to the size that the scar would be if a conventional (e.g., less durable) composition had been applied to the wound.

ADDITIONAL EMBODIMENTS

The following clauses are offered as further description of the disclosed invention:

1. A wound-care composition comprising:

a substrate;

optionally potassium alum, optionally wherein the potassium alum is potassium alum power;

and optionally urea;

optionally wherein the potassium alum makes up 10.27 wt. % of the composition within a tolerance of +/−50%;

optionally wherein the urea makes up 0.12 wt. % of the composition within a tolerance of +/−50%; and optionally wherein the components of the composition are combined, mixed, or any combination thereof; optionally wherein the potassium alum and urea are combined with the substrate (e.g., mixed with the substrate, dispersed in the substrate, or any combination thereof, for example, by mixing under conditions to provide the composition with increased homogeneity); optionally wherein the composition is approximately homogenous, substantially homogenous, essentially homogenous, or homogenous;

optionally wherein the substrate is spreadable;

optionally wherein the substrate is configured to adhere to and coat a wound;

optionally wherein the substrate is a liquid or partially liquid substrate;

optionally the substrate is configured and/or designed and/or adapted and/or formulated: to be or to make the composition hydrophobic, to be or to make the composition partially hydrophobic on a mass basis, to be or to make the composition substantially hydrophobic on a mass basis, to be or to make the composition approximately hydrophobic on a mass basis, to carry other components of the composition, to maintain the composition on a surface of a wound, to protect the composition, to maintain the other components of the composition on a surface of a wound, to provide durability to the composition, to provide displacement-resistance to the composition, to provide weather-resistance to the composition, to provide water-resistance to the composition, to be spreadable or to provide the composition with spreadability (e.g., at ambient conditions or 25° C.), to provide the composition with enough malleability or flowability to be applied to a wound by spreading the composition on the wound, to have or to provide the composition with a high enough viscosity or enough resistance to flowability so that the composition tends to remain in place after being applied to a wound (e.g., at ambient conditions or 25° C.), to provide any function disclosed for a substrate or component of a substrate in this disclosure, or any combination thereof;

optionally the composition is configured and/or designed and/or adapted and/or formulated: to be hydrophobic, to be partially hydrophobic on a mass basis, to be substantially hydrophobic on a mass basis, to be approximately hydrophobic on a mass basis, to carry other components of the composition, to remain on a surface of a wound, to protect a wound from contact by any object, to protect a wound from infection, to be durable, to be displacement-resistant, to be weather-resistant, to be water-resistant, to be spreadable (e.g., at ambient conditions or 25° C.), to have enough malleability or flowability to be applied to a wound by spreading the composition on the wound, to have a high enough viscosity or enough resistance to flowability that the composition tends to remain in place after being applied to a wound (e.g., at ambient conditions or 25° C.), to have a viscosity approximately equal to the viscosity of molasses (e.g., 5,000 to 10,000 cP) at 25° C., to have a viscosity approximately equal to the viscosity of honey (e.g., 10,000 cP) at 25° C., to have a viscosity between the viscosity of petrolatum (e.g., 4 to 20 cP) at 25° C. and the viscosity of honey (e.g., 10,000 cP) at 25° C., to have a viscosity between the viscosity of petrolatum (e.g., 4 to 20 cP) at 25° C. and the viscosity of molasses (e.g., 5,000 to 10,000 cP) at 25° C., to have a viscosity between the viscosity of petrolatum (e.g., 4 to 20 cP) at 25° C. and the viscosity of pine tar (e.g., 300 to 2500 cP) at 25° C., to provide any function disclosed for a composition or component of a composition in this disclosure, or any combination thereof; and optionally wherein the substrate is sufficiently adhesive and sufficiently viscous to adhere to the bottom of a horizontal, flat steel surface for 1 minute in air if a 1 mm, 3.175 mm, 4.5 mm, 6.35 mm, 12.7 mm, 1 mm to 12.7 mm, 3.175 mm to 12 mm (⅛ to ½ inch) 3.175 to 6.35 mm (⅛ to ¼ inch) or 6.35 to 12.7 mm (¼ to ½ inch) thick layer of the substrate is applied to a surface area on the bottom of the horizontal, flat steel surface, the surface area being 1 cm^2 or at least 1 cm^2 in area, wherein during the 1 minute, the air and the substrate are maintained at 101.325 kPa and at a temperature of 25° C.

2. The composition of any preceding clause, the composition (e.g., the substrate) comprising wood tar, optionally wherein the wood tar makes up 38.87 wt. % of the composition within a tolerance of +/−50%, optionally wherein the wood tar is pine tar.

3. The composition of any preceding clause, the composition (e.g., the substrate) comprising petrolatum, optionally wherein the petrolatum makes up 9.29 wt. % of the composition within a tolerance of +/−50%, optionally wherein the petrolatum is white petrolatum, optionally wherein the petrolatum is white petrolatum USP.

4. The composition of any preceding clause, optionally the composition comprising at least one antiseptic, at least one antibacterial, at least one antiviral, at least one fungicide, at least one nematicide, at least one pain reliever, at least one base, at least one solvent, or any combination thereof;

optionally the at least one antiseptic comprising povidone-iodine, acriflavin, methyl violet, ethyl alcohol, or any combination thereof;

optionally the at least one antibacterial comprising nitrofurazone, methyl violet, ethyl alcohol, or any combination thereof;

optionally the at least one antiviral comprising povidone-iodine, ethyl alcohol or any combination thereof;

optionally the at least one fungicide comprising povidone-iodine, methyl violet, furfural, ethyl alcohol, or any combination thereof;

optionally the at least one nematicide comprising methyl violet, furfural, or any combination thereof;

optionally wherein the povidone-iodine makes up 0.97 wt. % of the composition within a tolerance of +/−50%, optionally wherein the povidone-iodine is combined with (e.g., mixed with, dispersed in, or any combination thereof) C12-13 Pareth-9;

optionally wherein the acriflavin makes up 0.002 wt. % of the composition within a tolerance of +/−50%, optionally wherein the acriflavin (e.g., $C_{27}H_{25}ClN_6$) is a mixture of 3,6-Diamino-10-methylacridinium chloride (i.e., $C_{14}H_{14}ClN_3$) and 3,6-acridinediamine (i.e., $C_{13}H_{11}N_3$);

optionally wherein the methyl violet makes up 0.03 wt. % of the composition within a tolerance of +/−50%; optionally wherein the methyl violet is Methyl Violet 2B, Methyl Violet 6B, Methyl Violet 10B or any combination thereof;

optionally wherein the nitrofurazone makes up 0.04 wt. % of the composition within a tolerance of +/−50%, optionally wherein the nitrofurazone is combined with (e.g., mixed with, dispersed in, or any combination thereof) polyethylene glycols (e.g., water soluble polyethylene glycols);

optionally wherein the furfural makes up 0.04 wt. % of the composition within a tolerance of +/−50%, optionally wherein the furfural is provided to the composition by adding technical furfural to other components of the composition or adding a furfural composition that is at least 99.7 wt. % furfural to other components of the composition;

optionally the composition comprising the pain reliever, optionally wherein the pain reliever is lidocaine HCl, optionally wherein lidocaine HCl makes up 0.05 wt. % of the composition within a tolerance of +/−50%, optionally the lidocaine HCl is combined with (e.g., mixed with, dispersed in, or any combination thereof) water;

optionally the at least one solvent, at least one base or combination thereof comprises: at least one alcohol, water, C12-13 Pareth-9, propylene glycols or any combination thereof;

optionally the composition comprises ethyl alcohol, optionally wherein ethyl alcohol makes up 1 to 4 wt. % or 1, 2, 3 or 4 wt. % of the composition within a tolerance of +/−50%;

optionally the composition comprises water, optionally wherein water makes up 2 to 10 wt. % or 2, 3, 4, 5, 6, 7, 8, 9 or 10 wt. % of the composition within a tolerance of +/−50%;

optionally the composition comprises C12-13 Pareth-9, optionally wherein C12-13 Pareth-9 makes up 1 to 8 wt. % or 1, 2, 3, 4, 5, 6, 7 or 8 wt. % of the composition within a tolerance of +/−50%; and optionally the composition comprises at least one polyethylene glycol, optionally wherein the at least one polyethylene glycol or polyethylene glycols make up 18.7 wt. % of the composition within a tolerance of +/−50%.

5. The composition of any preceding clause, wherein, for at least one component of the composition, the tolerance is +/−45%, +/−40%, +/−35%, +/−30%, +/−25%, +/−20%, +/−15%, +/−10%, +/−9%, +/−8%, +/−7%, +/−6%, +/−5%, +/−4%, +/−3%, +/−2 or +/−1%, optionally wherein the at least one component is selected from the group consisting of the lidocaine HCl, the povidone-iodine, the petrolatum, the wood tar (e.g., pine tar), the potassium alum, the nitrofurazone, the acriflavin, the methyl violet, the furfural, the urea, the ethyl alcohol, the water, the C12-13 Pareth-9, the at least one polyethylene glycol, the polyethylene glycols or any combination thereof.

6. The composition of any preceding clause, the composition formulated to provide a reduction in scarring in a wound on a horse when a layer of the composition is topically applied to the wound within 1, 2, 3, 4, 6, 12, or 24 hours of the time that the wound occurred, wherein the reduction in scarring is deemed to be achieved if:

the layer of the composition is applied to a treated portion of the wound and the treated portion of the wound is covered with a first bandage;

a second bandage is applied to an untreated portion of the wound that is not treated by application of the composition, the second bandage being identical to the first bandage, and dimensions (e.g., length, width, area, shape or any combination thereof) of the untreated portion and the treated portion are equal;

every 24, 48, 72, 96, 120, 144, or 168 hours: the first bandage or a replacement bandage for the first bandage is removed from the treated portion of the wound, a new layer of the composition is applied to the treated portion of the wound, and the treated portion of the wound is covered with a replacement bandage for the first bandage;

every 24, 48, 72, 96, 120, 144, or 168 hours: the second bandage or a replacement bandage for the second bandage is removed from the untreated portion of the wound, and the untreated portion of the wound is covered with a replacement bandage for the second bandage; and 30 days after the application of the composition, the area of scar tissue corresponding to the treated portion of the wound is smaller than (e.g., no more than 95%, 90%, 80%, 70%, 60%, 50%, 40%, 30%, 20%, 10% or 5% of) the area of scar tissue corresponding to the untreated portion of the wound.

7. The composition of any preceding clause, comprising additional ingredients selected from the group consisting of water, propylene glycol, glycerin, Aloe barbadensis leaf juice, triethanolamine, isopropyl alcohol, polysorbate 80, carbomer, phenoxyethanol, benzyl alcohol, menthol, disodium EDTA, blue 1, yellow 5, C12-13 Pareth-9, citric acid, disodium phosphate, sodium hydroxide, water soluble polyethylene glycols, ethyl alcohol, and sodium propionate.

8. A method comprising: applying the composition of any preceding clause to a wound (e.g., open wound, cut, abrasion, puncture, break in the skin, opening in the skin or any combination thereof) on an animal (e.g., non-human, mammal, or any combination thereof) that is not intended for human consumption.

9. A method or the method of any preceding clause, the method comprising: applying the composition of any preceding clause to a wound on a horse.

10. The method of any preceding clause comprising: using the composition to facilitate healing (e.g., reducing the risk of infection, avoiding infection, killing, neutralizing or deactivating pathogens so that they cannot cause infection, promoting healthy tissue growth, promoting repair of the skin, reducing scarring, avoiding scarring or any combination thereof) at the location of the wound on the animal (e.g., horse, non-human, mammal or any combination thereof).

When an embodiment is described in this disclosure as comprising some element or group of elements, additional embodiments can consist essentially of or consist of the element or group of elements. Also, although the open-ended term "comprises" is generally used herein, additional embodiments can be formed by replacing the term "comprising" with the term "consisting essentially of" or the term "consisting of."

Where language, for example, "for" or "to", is used herein in conjunction with an effect, function, use or purpose, an additional embodiment can be provided by substituting "for" or "to" with "configured for/to" or "adapted for/to."

Additionally, when a range for a particular variable is given for an embodiment, an additional embodiment can be created using a subrange or individual values that are contained within the range. Moreover, when a value, values, a range, or ranges for a particular variable are given for one or more embodiments, an additional embodiment can be created by forming a new range whose endpoints are selected from any expressly listed value, any value between expressly listed values, and any value contained in a listed range. For example, if the application were to disclose an embodiment in which a variable is 1 and a second embodiment in which the variable is 3-5, a third embodiment can be created in which the variable is 1.31-4.23. Similarly, a fourth embodiment can be created in which the variable is 1-5.

As used herein, a tolerance of +/−Y % with respect to a value X refers to a range whose endpoints are X−(Y/100*X) and X+(Y/100*X). For example, if a component makes up 10 wt. % of the composition within a tolerance of +/−50%, then the component makes up 5 to 15 wt. % of the composition.

As used herein, examples of "substantially" include: "more so than not," "mostly," and "at least 30%, 40%, 50%, 60%, 70%, 80%, 90%, 95%, 96%, 97%, 98% or 99%" with respect to a referenced characteristic.

As used herein, examples of "about" and "approximately" include a specified value or characteristic to within plus or minus 30%, 25%, 20%, 15%, 10%, 9%, 8%, 7%, 6%, 5%, 4%, 3%, 2%, or 1% of the specified value or characteristic.

Unless otherwise specified or evident from context, percentages of a component in a composition are given in terms of weight percentages.

While this invention has been particularly shown and described with reference to preferred embodiments, it will be understood by those skilled in the art that various changes in form and detail may be made therein without departing from the spirit and scope of the invention. The inventors expect skilled artisans to employ such variations as appropriate, and the inventors intend the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A wound-care composition comprising:
a substrate comprising pine tar and petrolatum, wherein the pine tar makes up 38.87 wt. % of the composition within a tolerance of +− 50%, and wherein the petrolatum makes up 9.29 wt. % of the composition within a tolerance of +/− 50%;
potassium alum; and
urea;
wherein the potassium alum makes up 10.27 wt. % of the composition within a tolerance of +/− 50%; and
wherein the urea makes up 0.12 wt. % of the composition within a tolerance of +/− 50%.

2. The composition of claim 1, the potassium alum being a potassium alum powder.

3. The composition of claim 1, the composition further comprising at least one antiseptic, the at least one antiseptic comprising povidone-iodine, acriflavin, methyl violet, ethyl alcohol, or any combination thereof.

4. The composition of claim 3, the composition further comprising at least one antibacterial, the at least one antibacterial comprising nitrofurazone, methyl violet, ethyl alcohol, or any combination thereof.

5. The composition of claim 4, the composition further comprising at least one antiviral, the at least one antiviral comprising povidone-iodine, ethyl alcohol or any combination thereof.

6. The composition of claim 5, the composition further comprising at least one fungicide, the at least one fungicide comprising povidone-iodine, methyl violet, furfural, ethyl alcohol, or any combination thereof.

7. The composition of claim 6, the composition further comprising at least one nematicide, the at least one nematicide comprising methyl violet, furfural, or any combination thereof.

8. The composition of claim 7, the composition further comprising at least one pain reliever.

9. The composition of claim 8, wherein the povidone-iodine makes up 0.97 wt. % of the composition within a tolerance of +/− 50%.

10. The composition of claim 8, wherein the acriflavin makes up 0.002 wt. % of the composition within a tolerance of +/− 50%, wherein the acriflavin is a mixture of 3,6-Diamino-10-methylacridinium chloride and 3,6-acridinediamine.

11. The composition of claim 8, wherein the methyl violet makes up 0.03 wt. % of the composition within a tolerance of +/− 50%; wherein the methyl violet is Methyl Violet 2B, Methyl Violet 6B, Methyl Violet 10B or any combination thereof.

12. The composition of claim 8, wherein the nitrofurazone makes up 0.04 wt. % of the composition within a tolerance of +/− 50%.

13. The composition of claim 8, wherein the furfural makes up 0.04 wt. % of the composition within a tolerance of +/− 50%.

14. The composition of claim 8, wherein the pain reliever is lidocaine HCl, wherein lidocaine HCl makes up 0.05 wt. % of the composition within a tolerance of +/− 50%.

15. The composition of claim 8, wherein ethyl alcohol makes up 1 to 4 wt. % of the composition;
wherein the composition further comprises water, wherein the water makes up 2 to 10 wt. % of the composition;
wherein the composition further comprises C12-13 Pareth-9, wherein the C12-13 Pareth-9 makes up 1 to 8 wt. % of the composition; and
the composition further comprises at least one polyethylene glycol, wherein the at least one polyethylene glycol makes up 18.7 wt. % of the composition within a tolerance of +/− 50%.

16. The composition of claim 1, the composition formulated to provide a reduction in scarring in a wound on a horse when a layer of the composition is topically applied to the wound within 24 hours of the time that the wound occurred, wherein the reduction in scarring is deemed to be achieved if:
the layer of the composition is applied to a treated portion of the wound and the treated portion of the wound is covered with a first bandage;
a second bandage is applied to an untreated portion of the wound that is not treated by application of the composition, the second bandage being identical to the first bandage, the areas of the treated portion of the wound and the untreated portion of the wound being equal;
every 24 hours: the first bandage or a replacement bandage for the first bandage is removed from the treated portion of the wound, a new layer of the composition is applied to the treated portion of the wound, and the treated portion of the wound is covered with a replacement bandage for the first bandage;
every 24 hours: the second bandage or a replacement bandage for the second bandage is removed from the untreated portion of the wound, and the untreated portion of the wound is covered with a replacement bandage for the second bandage; and
30 days after the application of the composition, the area of scar tissue corresponding to the treated portion of the wound is smaller than the area of scar tissue corresponding to the untreated portion of the wound.

17. The composition of claim 1, the composition further comprising additional ingredients selected from the group consisting of water, propylene glycol, glycerin, Aloe barbadensis leaf juice, triethanolamine, isopropyl alcohol, polysorbate 80, carbomer, phenoxyethanol, benzyl alcohol, menthol, disodium EDTA, blue 1, yellow 5, C12-13 Pareth-9, citric acid, disodium phosphate, sodium hydroxide, water soluble polyethylene glycols, ethyl alcohol, and sodium propionate.

18. A method comprising:
applying the composition of claim 1 to a wound on a non-human animal.

19. The method of claim 18 comprising:
using the composition to promote healing at the location of the wound on the non-human animal.

* * * * *